US012564829B2

(12) United States Patent
Bouchard et al.

(10) Patent No.: US 12,564,829 B2
(45) Date of Patent: *Mar. 3, 2026

(54) BIOLOGICALLY APPLICABLE WATER-SOLUBLE HETEROGENEOUS CATALYSTS FOR PARA-HYDROGEN INDUCED POLARIZATION

(71) Applicants: THE REGENTS OF THE UNIVERSITY OF CALIFORNIA, Oakland, CA (US); CEDARS-SINAI MEDICAL CENTER, Los Angeles, CA (US)

(72) Inventors: Louis Bouchard, Los Angeles, CA (US); Shawn Wagner, Altadena, CA (US); Stefan Gloeggler, Bordeaux (FR)

(73) Assignees: THE REGENTS OF THE UNIVERSITY OF CALIFORNIA, Oakland, CA (US); CEDARS-SINAI MEDICAL CENTER, Los Angeles, CA (US)

( * ) Notice: Subject to any disclaimer, the term of this patent is extended or adjusted under 35 U.S.C. 154(b) by 302 days.

This patent is subject to a terminal disclaimer.

(21) Appl. No.: 17/694,560

(22) Filed: Mar. 14, 2022

(65) Prior Publication Data

US 2022/0323946 A1 Oct. 13, 2022

Related U.S. Application Data

(63) Continuation of application No. 15/799,498, filed on Oct. 31, 2017, now Pat. No. 11,273,431.

(60) Provisional application No. 62/415,986, filed on Nov. 1, 2016.

(51) Int. Cl.

| | |
|---|---|
| ***B01J 23/40*** | (2006.01) |
| ***A61K 49/10*** | (2006.01) |
| ***B01J 23/42*** | (2006.01) |
| ***B01J 29/03*** | (2006.01) |
| ***B01J 29/08*** | (2006.01) |
| ***B01J 29/40*** | (2006.01) |
| ***B01J 29/44*** | (2006.01) |
| ***B01J 29/70*** | (2006.01) |
| ***B01J 29/80*** | (2006.01) |
| ***B01J 29/89*** | (2006.01) |
| ***B01J 31/16*** | (2006.01) |
| ***B01J 35/30*** | (2024.01) |
| ***B01J 35/45*** | (2024.01) |
| ***B01J 35/51*** | (2024.01) |
| ***B01J 35/61*** | (2024.01) |
| ***B01J 35/63*** | (2024.01) |
| ***B01J 35/64*** | (2024.01) |
| ***B01J 37/00*** | (2006.01) |
| ***B01J 37/02*** | (2006.01) |
| ***B01J 37/03*** | (2006.01) |
| ***B01J 37/16*** | (2006.01) |
| ***C07C 67/303*** | (2006.01) |

(52) U.S. Cl.

CPC ........... *B01J 31/1625* (2013.01); *A61K 49/10* (2013.01); *B01J 23/42* (2013.01); *B01J 29/0308* (2013.01); *B01J 29/084* (2013.01); *B01J 29/40* (2013.01); *B01J 29/44* (2013.01); *B01J 29/7007* (2013.01); *B01J 29/80* (2013.01); *B01J 29/89* (2013.01); *B01J 35/397* (2024.01); *B01J 35/45* (2024.01); *B01J 35/51* (2024.01); *B01J 35/615* (2024.01); *B01J 35/633* (2024.01); *B01J 35/647* (2024.01); *B01J 37/0018* (2013.01); *B01J 37/0221* (2013.01); *B01J 37/031* (2013.01); *B01J 37/16* (2013.01); *C07C 67/303* (2013.01); *B01J 2229/186* (2013.01); *B01J 2231/645* (2013.01); *B01J 2235/00* (2024.01); *B01J 2235/05* (2024.01); *B01J 2235/30* (2024.01); *B01J 2531/0222* (2013.01); *B01J 2531/0275* (2013.01); *B01J 2531/828* (2013.01)

(58) Field of Classification Search

CPC .. B01J 31/1625; B01J 23/42; B01J 2531/828; B01J 35/45; A61K 49/10

See application file for complete search history.

(56) References Cited

U.S. PATENT DOCUMENTS 11,273,431 B2 * 3/2022 Bouchard .............. B01J 35/647
2014/0125334 A1 5/2014 Owers-Bradley et al.

OTHER PUBLICATIONS

S. Campisi, et al. 6 Catalysts 185 (2016) (Year: 2016).*
D. Ling, et al., 9 Nano Today, 457-477 (2014) (Year: 2014).*
S. Glöggler, et al., 52 Chemical Communications 605-608 (2015) (Year: 2015).*
S. Glöggler, et al., 54 Angewandte Chemie International Edition 2452-2456( 2015) (Year: 2015).*
I. Koptyug et al., 129 Journal of the American Chemical Society, 5580-5586 (2007) (Year: 2007).*
Bowers et al., 57 Physical Review Letters, 2645-2648 (1986) (Year: 1986).*

(Continued)

*Primary Examiner* — Alexander R Pagano
*Assistant Examiner* — Frank S. Hou
(74) *Attorney, Agent, or Firm* — Foley & Lardner LLP

(57) ABSTRACT

A heterogeneous catalyst composition for para-hydrogen induced polarization includes ligand-capped nanoparticles dispersed in water. The ligand-capped nanoparticles include metal nanoparticles that are surface functionalized with organic ligands, a molecular weight of the organic ligands is no greater than 300 g/mol, and the organic ligands each includes multiple binding moieties as coordinates sites for binding to a nanoparticle surface.

13 Claims, 11 Drawing Sheets

(56) References Cited

OTHER PUBLICATIONS

K. Kovtunov et al., 59 Topics in Catalysis, 1686-1699 (2016) (Year: 2016).*
S. Kunz et al., 15 Physical Chemistry Chemical Physics, (2013) (Year: 2013).*
M. Auffan et al., 4 Nature Nanotechnology, 634-641 (2009) (Year: 2009).*
Anuji Abraham, "1H MAS NMR Study of Cysteine-Coated Gold Nanoparticles", J. Phys. Chem B. 2012, dated 2012, pp. 7771-7775.
Cappallari et al. "Synthesis of ultra-small cysteine-capped gold nanoparticles by pH switching of the Au(I)-cysteine polymer." Journal of Colloid and Interface Science 441, 17-24 (2015).
Liang, Shuyan "Water-Soluble L-Cysteine-Coated." International Journal of Nanomedicine. 2325-2333 (2015).
We et al. "Citrate-Capped Platinum Nanoparticle as a Smart Probe for Ultrasensitive Mercury Sensing." Anal. Chem. 86, 10955-10960 (2014).

* cited by examiner

BIOLOGICALLY APPLICABLE WATER-SOLUBLE HETEROGENEOUS CATALYSTS FOR PARA-HYDROGEN INDUCED POLARIZATION

CROSS-REFERENCE TO RELATED APPLICATION

This application is a continuation of U.S. application Ser. No. 15/799,498, filed Oct. 31, 2017; which claims the benefit of U.S. Provisional Application No. 62/415,986, filed Nov. 1, 2016, the content of each of which are incorporated herein by reference in their entirety.

TECHNICAL FIELD

This disclosure generally relates to heterogeneous catalysts that are water-soluble and can yield high polarization of substrate molecules.

BACKGROUND

Nuclear magnetic resonance (NMR) hyperpolarization aims to overcome a low signal of NMR by increasing spin polarization up to four orders of magnitude compared to thermal polarizations from state-of-the-art superconducting magnets. Hyperpolarization techniques include spin exchange optical pumping, the more established technique of dynamic nuclear polarization (DNP), and the use of para-hydrogen induced polarization (PHIP) or Signal Amplification by Reversible Exchange (SABRE). Polarization techniques depend on the context and application. Each technique can potentially lead to the development of promising contrast agents for biomedical imaging, with an example of dissolution DNP for which in vivo human use has been demonstrated. To generate hyperpolarization using PHIP or SABRE, a para-enriched spin state of hydrogen is first created by passing hydrogen over a catalyst at low temperatures, generating close to 100% para-state below about 25 K. The nearly pure stable singlet spin state of para-hydrogen can subsequently be utilized to hyperpolarize a molecule of interest by an addition reaction or by a catalyst-mediated, reversible exchange process.

PHIP hyperpolarized substrates have been proposed as contrast agents for angiography or cancer detection. A major drawback is that the generation of sufficiently high nuclear spin polarization in biocompatible solvents is obtained using a homogeneous catalyst. However, homogeneous catalysts raise biotoxicity concerns, since the homogeneous catalysts cannot be readily separated from a solution. Without sufficient separation, a hyperpolarized molecule is mixed with a homogeneous catalyst, and the presence of the catalyst in solution can pose toxicity issues, particularly if heavy metals are used, such as rhodium. Although a preliminary study has shown that a state-of-the-art homogeneous catalyst produces subclinical hepatic and renal toxicity in rats, further studies remain to clarify toxicity concerns. To address such concerns, approaches are desired in which a catalyst can be separated from a potential molecular imaging agent. One such approach is a phase separation technique in which a nuclear-spin polarization is generated in water followed by extraction of a substrate of interest. The extraction process, however, represents a stage during which the generated polarization inevitably decays and a loss in polarization results. Attempts have been made to develop heterogeneous catalysts, but these typically operate in non-biocompatible solvents, yield low polarizations in water, and suffer from leaching problems where immobilized ligands leach in solution.

It is against this background that a need arose to develop the embodiments described herein.

SUMMARY

Embodiments of this disclosure are directed to nanoparticle-based catalysts that are water-soluble and can yield high polarization of substrate molecules via PHIP. In some embodiments, cysteine-capped platinum nanoparticles serve as a heterogeneous catalyst which yields large polarization by PHIP in water. The use of water as a solvent promotes biocompatibility. Moreover, the use of a heterogeneous catalyst also promotes biocompatibility: ligand-capped nanoparticles can be immobilized on a solid support, and the nanoparticles also can be filtered using, for example, a filtration membrane. Ligand-capped nanoparticles of embodiments of this disclosure can be used to generate nuclear-spin polarized molecules for in vivo biological applications, such as medical imaging applications for magnetic resonance imaging (MRI) detection.

Advantageously, ligand-capped nanoparticles of embodiments of this disclosure can be used to generate high polarization under conditions that favor biocompatibility and water solubility. Specifically, a selection of ligands renders the nanoparticles water-soluble or dispersible in water. Also, a relatively high surface coverage of the nanoparticles by the ligands favors pair-wise hydrogenation, which is a condition for generating strong nuclear-spin polarization by PHIP. Further, the use of the ligand-capped nanoparticles as a heterogeneous catalyst addresses a separation issue: polarized molecules can be readily separated from the heterogeneous catalyst through a filtration stage to remove the catalyst. As another option, the nanoparticles can be immobilized on a solid support (e.g., silica or alumina), and the solid support can remain in a reactor and does not flow with a liquid phase. As a further option, the nanoparticles can be bound to larger sized water-soluble or dispersible particles. For example, the larger sized particles can be polystyrene beads (or other polymeric beads) having sizes of about 500 nm and which are dispersible in water or heavy water. More generally, the larger sized particles can have sizes (e.g., in terms of a diameter or another lateral dimension) in a range of about 200 nm to about 10 μm, about 200 nm to about 5 μm, or about 200 nm to about 1 μm.

In an aspect according to some embodiments, a heterogeneous catalyst composition for PHIP includes nanoparticles that are capped or surface functionalized with ligands.

In some embodiments, the nanoparticles are metal nanoparticles which are formed of, or include, a metal, such as a platinum group metal (platinum, rhodium, ruthenium, iridium, osmium, or palladium), or another transition metal. Metal nanoparticles which are formed of, or include, a combination of two or more different metals, such as in the form of an alloy or a mixture, are also encompassed by this disclosure. In some embodiments, the nanoparticles have sizes (e.g., in terms of a diameter or another lateral dimension) in a range of about 0.5 nm to about 100 nm, about 0.5 nm to about 80 nm, about 0.5 nm to about 50 nm, about 0.5 nm to about 30 nm, about 0.5 nm to about 10 nm, or about 0.5 nm to about 5 nm. In some embodiments, at least one of the nanoparticles has a size (e.g., in terms of a diameter or another lateral dimension) in a range of about 0.5 nm to about 100 nm, about 0.5 nm to about 80 nm, about 0.5 nm to about 50 nm, about 0.5 nm to about 30 nm, about 0.5 nm to about 10 nm, or about 0.5 nm to about 5 nm. In some embodiments, the nanoparticles have an average size (e.g., in terms of an average diameter or another lateral dimension) in a range of about 0.5 nm to about 100 nm, about 0.5 nm to about 80 nm, about 0.5 nm to about 50 nm, about 0.5 nm to about 30 nm, about 0.5 nm to about 10 nm, about 0.8 nm to about 10 nm, about 0.5 nm to about 5 nm, about 0.8 nm to about 5 nm, about 0.8 nm to about 4 nm, about 0.8 nm to about 3 nm, about 0.8 nm to about 2.5 nm, or about 0.8 nm to about 2 nm. In some embodiments, the nanoparticles are generally spherical or spheroidal with aspect ratios of about 3 or less, about 2 or less, or about 1.5 or less, although nanostructures having other shapes and aspect ratios are also encompassed by this disclosure, such as aspect ratios greater than about 3.

In some embodiments, the ligands are organic ligands. In some embodiments, the ligands are homogeneous with respect to one another, although the use of different ligands is also encompassed by this disclosure. In some embodiments, the ligands are hydrophilic, and each includes at least one hydrophilic moiety. Examples of suitable hydrophilic moieties include carboxyl group, hydroxyl group, carbonyl group, sulfhydryl (or thiol) group, amino group, phosphate group, and charged forms thereof. In some embodiments, the ligands each includes multiple (e.g., two or more) binding moieties as coordinates sites for binding to a nanoparticle surface. Examples of suitable binding moieties include sulfhydryl (or thiol) group, amino group, and charged forms thereof. In some embodiments, the ligands each includes sulfhydryl (or thiol) group and amino group as binding moieties, and further includes at least one hydrophilic moiety. In some embodiments, the ligands are, or include, amino acids. In some embodiments, the ligands each consists of, or consists essentially of, an amino acid. In some embodiments, the ligands are, or include, cysteine, such as L-cysteine.

In some embodiments, the composition includes a weight content of the ligands of at least about 5 wt. % relative to a combined weight of the nanoparticles and the ligands, such as about 8 wt. % or greater, about 10 wt. % or greater, about 12 wt. % or greater, about 14 wt. % or greater, or about 16 wt. % or greater, and up to about 24 wt. % or greater. In some embodiments, a surface coverage of the nanoparticles by the ligands is at least about 4.2 ligands per $nm^2$, such as about 4.4 ligands per $nm^2$ or higher, about 4.6 ligands per $nm^2$ or higher, about 4.8 ligands per $nm^2$ or higher, about 5 ligands per $nm^2$ or higher, about 5.5 ligands per $nm^2$ or higher, about 6 ligands per $nm^2$ or higher, about 6.5 ligands per $nm^2$ or higher, about 7 ligands per $nm^2$ or higher, about 7.5 ligands per $nm^2$ or higher, or about 8 ligands per $nm^2$ or higher, and up to about 8.4 ligands per $nm^2$ or higher. In some embodiments, a surface coverage of the nanoparticles by the ligands is at least about 0.8 mol/g in terms of moles of the ligands relative to a combined weight of the nanoparticles and the ligands, such as about 0.85 mol/g or higher, about 0.9 mol/g or higher, about 0.95 mol/g or higher, about 1 mol/g or higher, about 1.05 mol/g or higher, about 1.1 mol/g or higher, about 1.15 mol/g or higher, about 1.2 mol/g or higher, about 1.25 mol/g or higher, about 1.3 mol/g or higher, or about 1.35 mol/g or higher, and up to about 1.5 mol/g or higher. In some embodiments, a molecular weight of the ligands is no greater than about 300 g/mol, such as about 280 g/mol or less, about 250 g/mol or less, about 230 g/mol or less, about 200 g/mol or less, about 180 g/mol or less, about 150 g/mol or less, or about 130 g/mol or less.

In some embodiments, the composition includes a solvent, and the ligand-capped nanoparticles are dispersed in the solvent. In some embodiments, the solvent is water. In some embodiments, the solvent is heavy water or $D_2O$. In some embodiments, a concentration of the ligand-capped nanoparticles is in a range of about 1 mg/mL to about 20 mg/mL, about 2 mg/mL to about 15 mg/mL, about 5 mg/mL to about 15 mg/mL, or about 10 mg/mL. In some embodiments, the composition serves as a reagent for medical imaging. In some embodiments, an organic substrate (including substrate molecules) is also included, either in a same container or compartment along with the ligand-capped nanoparticles dispersed in the solvent, or in a separate container or compartment of a medical imaging kit. In some embodiments, the organic substrate is, or includes, hydroxyethyl acrylate.

In another aspect according to some embodiments, a method for medical imaging includes combining ligand-capped nanoparticles and an organic substrate in a solvent, followed by hydrogenation and polarization of the organic substrate, in the presence of the ligand-capped nanoparticles, by flowing or pressurizing para-hydrogen gas, followed by removing the ligand-capped nanoparticles by filtration or in another manner, and followed by conveying the polarized organic substrate to a patient for medical imaging, such as in vivo MM.

In a further aspect according to some embodiments, a method for synthesis of ligand-capped nanoparticles includes combining a metal-containing precursor and ligands in a solvent, followed by reduction of the metal-containing precursor in the presence of a reducing agent. In some embodiments, the metal-containing precursor is a platinum group metal-containing precursor, such as hexachloroplatinic acid hexahydrate, and the ligands are, or include, cysteine, such as L-cysteine. In some embodiments, the reducing agent is, or includes, sodium borohydride. In some embodiments, a molar ratio of the metal-containing precursor to the ligands is in a range of about 1:2 to about 2:1, about 1:2 to about 1.5:1, about 1:1.5 to about 1.5:1, or about 1:1.

Other aspects and embodiments of this disclosure are also contemplated. The foregoing summary and the following detailed description are not meant to restrict this disclosure to any particular embodiment but are merely meant to describe some embodiments of this disclosure.

BRIEF DESCRIPTION OF THE DRAWINGS

For a better understanding of the nature and objects of some embodiments of this disclosure, reference should be made to the following detailed description taken in conjunction with the accompanying drawing.

DETAILED DESCRIPTION

Figure 1:
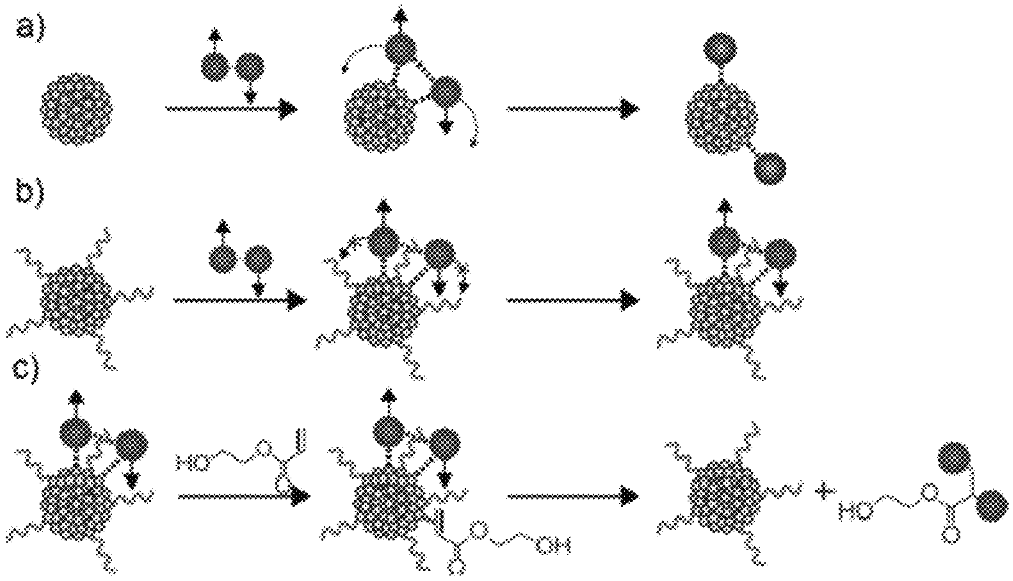
FIG. 1. (a) Para-hydrogen (circles with arrows represent hydrogen with quantum correlation) that adsorbs onto a surface of a bare platinum nanoparticle is prone to randomization processes leading to the loss of quantum correlation. (b) If ligands are attached to the surface of the nanoparticle (wavy lines), the randomization can be reduced, resulting in preservation of the singlet state between the two protons. (c) As a result of the preserved singlet state on the surface of the capped nanoparticle, para-hydrogen can be used to generate hyperpolarized products in water.

To address biotoxicity concerns associated with the use of homogeneous catalysts and polarization decay associated with an extraction process following generation of polarization in organic solvents, the use of heterogeneous PHIP or SABRE catalyst is a desirable strategy to generate a highly pure substrate, since the catalyst can be readily filtered or immobilized to avoid contamination. For in vivo applications the use of biocompatible solvents, such as water in combination with a heterogeneous catalyst is desirable. For example, glutathione-capped platinum nanoparticles dispersed in water can be used to generate hyperpolarization. These glutathione-capped platinum nanoparticles provide a heterogeneous PHIP catalyst in water yielding significant polarization of dissolved molecules that remain in a liquid phase; however, measured levels of proton polarization of hydroxyethyl propionate (HEP) are still relatively low (e.g., P=about 0.25%) compared to the levels desired for in vivo applications (e.g., P>about 1%). Higher polarization can be achieved by capped nanoparticles based on an insight that the mobility of hydrogen atoms is reduced by ligands, thereby favoring a pair-wise addition mechanism (see FIG. 1).

In accordance with some embodiments of this disclose, cysteine-capped platinum nanoparticles are presented as substantially improved catalysts yielding average proton polarizations of P=about 0.65% (or higher) in water. In comparison, levels of P=1.26% are achieved with a homogeneous catalyst performing a same experiment using similar conditions and setup. Thus, the heterogeneous catalyst is competitive with state-of-the-art homogeneous catalyst for hyperpolarization in water. In a recycling experiment, it is demonstrated that these nanoparticles can be used 5 times (or more) without noticeable loss of polarization. It is further established that the properties of the ligands for capping the nanoparticles and the nanoparticles' surface coverage are particular factors for achieving high levels of polarization; indeed, these factors can be more important than achieving small particle sizes.

In some embodiments, two types of nanoparticles investigated are synthesized based on a platinum core capped with L-cysteine (Cys), and N-acetyl-L-cysteine (NAC) ligands, respectively. For the synthesis, hexachloroplatinic acid hexahydrate and the desired ligand were suspended in water and reduced with sodium borohydride, yielding ligand-capped nanoparticles (Scheme 1 a,b). In order to achieve nanoparticles with narrow size distributions, with N-acetyl-L-cysteine, a metal-containing precursor to ligand molar ratio of about 1:1.3 was used (NAC@Pt) and for L-cysteine, the molar ratio was about 1:1 or about 1:1.1 (Cys1@Pt and Cys1.1@Pt). Depending on the cysteine concentration, particles with two different average sizes were isolated: about 2.4 nm and about 1.4 nm. The average size for NAC@Pt was found to be about 1.9 nm as confirmed by transmission electron microscopy (TEM) (see Example section).

Scheme 1. a) Synthesis of cysteine-capped nanoparticales. b) Synthesis of N-acetylcysteine nanoparticles.

(a)

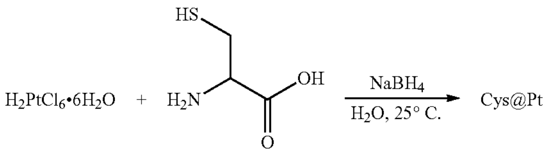

(b)

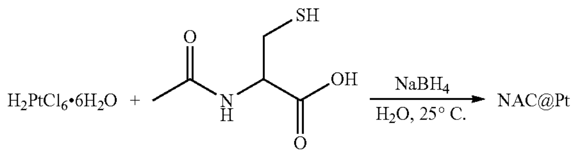

Figure 2:
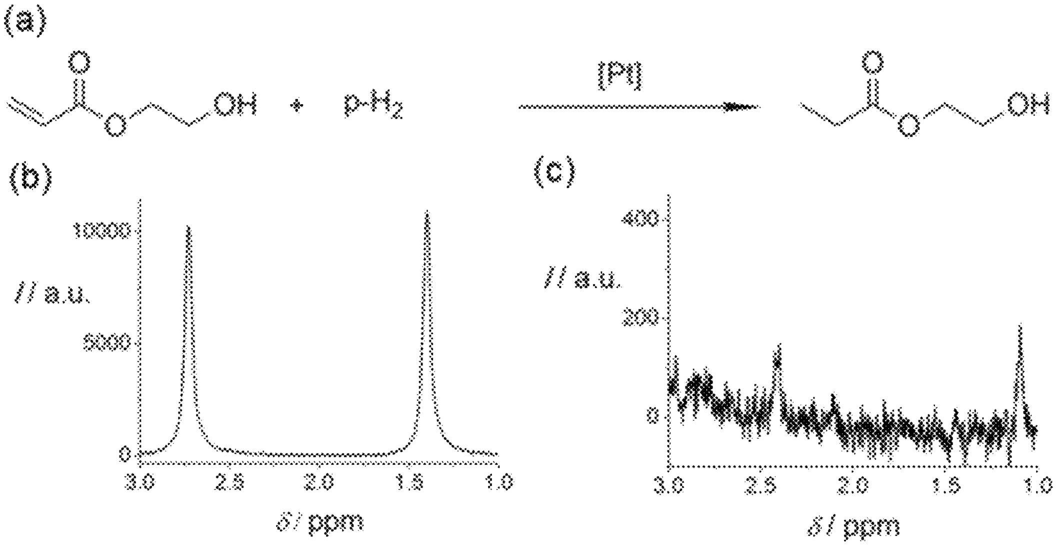
FIG. 2. (a) Reaction of hydroxyethyl acrylate (HEA) to hydroxyethyl propionate (HEP) utilizing para-hydrogen. (b) Hyperpolarized $^1H$ NMR spectrum shown in absolute values at $B_0$=about 14.1 T. (c) Thermal polarized $^1H$ NMR spectrum after the polarization at $B_0$=about 14.1 T. The signal enhancement in the shown spectrum accounts for =about 145, which corresponds to a polarization of P=about 0.7%.

In order to confirm the removal of residual platinum ions originating from the hexachloroplatinic acid, two experiments were conducted with all three nanoparticles: (1) Dilute samples with nanoparticles in water were characterized by ultraviolet/visible (UV/vis) spectroscopy and compared to the signal of hexachloroplatinic acid. For platinum ions, a characteristic absorbance of about 260 nm can be observed, which is the case for hexachloroplatinic acid but not for any of the synthesized nanoparticles. (2) A mercury poisoning experiment was performed in which the hydrogenation of hydroxyethyl acrylate (HEA) was initiated in separate experiments with the three different particles. Upon addition of mercury the hydrogenation stopped, establishing that the nanoparticles are catalyzing the reaction and not residual platinum ions. The ligand binding on the particles was validated by $^{1}H$ NMR, resulting in significant dipolar broadening of the ligands' resonances (see Example section). Furthermore, for all of the particle species, a ligand coverage of about 16 wt. % was confirmed by thermogravimetric analysis. Thus, substantially the same amount of platinum catalyzes a reaction if hyperpolarization experiments are performed with identical concentrations. Hyperpolarization experiments were conducted under inert gas with about 10 mg/mL particle concentrations, about 2 mg HEA and about 5 bar para-hydrogen in water at about 80° C. Hyperpolarized HEP shows two characteristic lines in the $^{1}H$ NMR spectrum at about 2.5 ppm and about 1.0 ppm (FIG. 2). On average, a polarization of P=about 0.65% was observed for both of the Cys@Pt particles, and a polarization of P=about 0.10% was achieved for NAC@Pt, in contrast to glutathione-capped platinum nanoparticles (GSH@Pt) reaching P=about 0.25%. A homogeneous catalyst is used under identical conditions and a proton polarization of about 1.26% is obtained, merely a factor of about two greater than the polarization achieved with the Cys@Pt particles. Typical conversions in the proton experiments were about 1% of the starting material. This experiment is, however, not optimized and the use of automatic polarizers should improve the conversion. Polarization transfer experiments from $^{1}H$ to $^{13}C$ nuclei with a custom-built polarizer led to about 10-fold (P=about 0.01%) signal enhancements and a conversion of about 50% in an about 3 s experiment. It is noted that this specific polarizer design was not optimized for heterogeneous experiments (see Example section). $^{13}C$ polarizations above about 50% of HEP can be achieved with automated polarizers utilizing a homogeneous catalyst. As the $^{1}H$ polarization is about twice as high as for the Cys@Pt nanoparticles, it is extrapolated that about 10-25% polarization should be attainable in an optimized device. This amount of polarization is sufficient for in vivo experiments. Consequently, the investigated particles can serve as a heterogeneous alternative to homogeneous catalysts.

Figure 3:
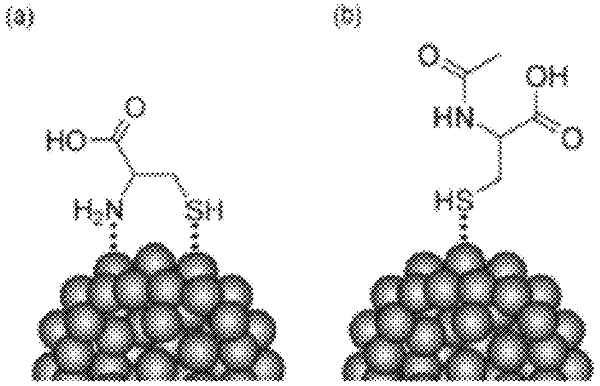
FIG. 3. (a) Schematic of cysteine coordination to a platinum particle. (b) Schematic of acetylcysteine coordination to a platinum particle. Due to a higher amount of coordination in Cys@Pt, less randomization process of the para-spin state of hydrogen on the particles surface can occur, leading to higher polarization.

Particle characteristics are summarized in Table 1. Due to the generally spherical shape of the nanoparticles, a cubo-octahedral structure can be assumed for which the amount of surface atoms can be estimated. The amount of ligands covering the surface was found to be the highest for Cys1@Pt, followed by NAC@Pt, Cys1.1@Pt and GSH@Pt. However, cysteine has two potential coordination sites to a particle's surface: a thiol group and an amino group. NAC is a derivative of cysteine with the amino group protected; thus, the amino group does not coordinate to the particle's surface and just the thiol group binds to the surface to stabilize the particle (FIG. 3). Other infrared investigations on GSH- and cysteine-capped platinum nanoparticles of larger size revealed that upon the ligands' interaction with the particle surface N—H and S—H vibrations vanish, which can be understood as an indication for binding. Overall, the cysteine ligands with higher coordination restrict the randomization processes of para-hydrogen on the particles' surfaces. As a result, the cysteine particles compared to acetylcysteine have about 6.5-fold increase in polarization. Other results for another dual coordination ligand, glutathione-capped platinum particles (GSH@Pt), support this interpretation. The ligand coverage of GSH@Pt by weight percentage is lower than NAC@Pt but still yields a higher polarization. With respect to the polarization, an increase can occur if fewer platinum sites are available on the particles' surfaces. Regarding the turnover frequency (TOF) of HEA and hydrogen at about 80° C. and about 1 atm hydrogen pressure, it was found that of the synthesized particles Cys1 @Pt show the highest reactivity, which is followed by Cys1.1@Pt and NAC@Pt. For the higher amount of ligands, a higher reaction rate is achieved and para-hydrogen can react faster with HEA. However, GSH@Pt shows a higher catalytic activity than the synthesized particles, although the achieved polarization is lower. GSH on a nanoparticle surface may allow for a better access for reactants to the surface due to their packing properties. A better interaction with the metal surface explains the higher conversion but may indicate that more randomization can occur due to the higher degree of hydrogen diffusion. Thus, a loss in polarization can be observed, which makes the Cys@Pt particles superior alternatives to generate polarization.

TABLE 1

Summary of particle characteristics.

| Particle | Ligands/ wt % | Ligands/ mol/g | Diameter/ nm | P/% | Ligands/ $nm^2$ (sphere) | Surface atoms/ per particle | TOF/$h^{-1}$ (80° C.) |
|---|---|---|---|---|---|---|---|
| NAC@Pt | 16 | 0.98 | 1.9 ± 0.4 | 0.1 | 4.8 | 138 | 3.0 |
| Cys1@Pt | 16 | 1.32 | 2.4 ± 0.5 | 0.65 | 8.4 | 256 | 31.8 |
| Cys1.1@Pt | 16 | 1.32 | 1.4 ± 0.3 | 0.65 | 4.7 | 67 | 11.0 |
| GSH@Pt[‡] | 23 | 0.75 | 2.0 | 0.25 | 4.1 | 155 | 87.8 |

A major advantage of heterogeneous catalysts over homogeneous catalysts is their recyclability. Particles can be filtered and reused if an achieved polarization remains substantially constant following repeated experiments. In order to test for the particles' recyclability, a particle concentration of about 15 mg/mL was used to produce hyperpolarized HEA five times. After each stage, the particles were centrifuged, and the supernatant solvent was removed. Subsequently, the particles were re-suspended in water and re-used to generate hyperpolarized HEP. For all three synthesized particles, the polarization measured was reproduced in consecutive experiments (see Example section).

In conclusion, synthesis is performed for two types of nanoparticles that are dispersible in water and highly effective in inducing hyperpolarization from para-hydrogen. Due to the optimization of ligand coverage and ligand-particle interaction, an increase in HEP polarization greater than about 2-fold was achieved in water compared to GSH@Pt particles. Experiments with two different sized nanoparticles indicate that the ligand coordinated to the particle's surface may play a more important role in generating hyperpolarization than the particle size itself. PHIP itself may therefore provide a method to investigate surface properties of ligand-capped nanoparticles. Additionally, the recyclability of the particles was successfully demonstrated through five consecutive uses without noticeable loss in polarization strength. Since the $^1H$ polarization obtained with the state-of-the-art homogeneous catalyst is just a factor of about 2 higher than the polarization achieved for the synthesized particles, the cysteine-based particles represent heterogeneous alternatives; their desired ability to mitigate toxicity issues makes them desirable candidates for a variety of clinical molecular imaging applications.

Example

The following example describes specific aspects of some embodiments of this disclosure to illustrate and provide a description for those of ordinary skill in the art. The example should not be construed as limiting this disclosure, as the example merely provides specific methodology useful in understanding and practicing some embodiments of this disclosure.

Materials and Methods

Chemicals

Hexachloroplatinic acid, sodium borohydride, absolute ethanol, cysteine and acetylcysteine were purchased from Sigma-Aldrich. $D_2O$ was purchased from Cambridge isotopes and all chemicals were used without further purification.

Methods for the Particle Characterization

NMR spectra were recorded on a Bruker AV600 or on a Bruker 94/20 Biospec with about 9.4 T. Transmission electron microscopy (TEM) was performed on a FEI Tecnai T12. Thermogravimetric analysis (TGA) was conducted using a Perkin Elmer Pyris Diamond TG/DTA from about 25° C. to about 650° C. UV/vis characterization was performed on an Agilent 8453 UV-vis spectrophotometer.

Synthetic Procedures

Unless otherwise noted, each synthetic stage was performed under inert gas atmosphere.

Synthesis of Acetylcysteine-Capped Platinum Nanoparticles (NAC@Pt)

About 98.4 mg (about 0.19 mmol) of hexachloroplatinic acid hexahydrate and about 40.3 mg (about 0.25 mmol) of acetylcysteine were dissolved in about 25 mL deoxygenated ultrapure water under argon atmosphere and stirred for about 30 minutes. Subsequently, about 74 mg (about 1.95 mmol) $NaBH_4$ dissolved in about 3 mL ultrapure water was added over about 1 minute under argon atmosphere. The brown suspension was stirred for about an additional hour, for about 3 hours under static vacuum and concentrated to near dryness. Particles were precipitated with about 30 mL deoxygenated, absolute ethanol. After about 30 minutes the ethanol was decanted and the particles dried under vacuum. Alternatively, the particles were centrifuged for about 30 minutes and the supernatant decanted followed by drying under vacuum. Further purification can be achieved by re-suspending the particles in water, centrifuging the suspension at about 109000 rpm for about 5 hours in an ultracentrifuge and removing the supernatant solvent followed by drying in vacuum.

Synthesis of Cysteine-Capped Platinum Nanoparticles (Cys@Pt)

About 98.4 mg (about 0.19 mmol) of hexachloroplatinic acid hexahydrate and either about 23.0 mg (about 0.19 mmol) or about 25.3 mg (about 0.21 mmol) of L-cysteine were suspended in about 25 mL deoxygenated ultrapure water under argon atmosphere and stirred for about 30 minutes. Subsequently, about 74 mg (about 1.95 mmol) $NaBH_4$ dissolved in about 3 mL ultrapure water was added over about 1 minute under argon atmosphere. The brown suspension was stirred for about an additional hour, for about 3 hours under static vacuum and concentrated to near dryness. Particles were precipitated with about 30 mL deoxygenated, absolute ethanol. After about 30 minutes the ethanol was decanted and the particles dried under vacuum. Alternatively, the particles were centrifuged for about 30 minutes and the supernatant decanted followed by drying under vacuum. If a platinum precursor to cysteine molar ratio of about 1:1 was used, Cys1@Pt platinum particles were yielded and if a molar ratio of about 1:1.1 was used, Cys1.1@Pt particles were obtained.

Characterization of the Nanoparticles

Particle Distribution and UV/Vis

Figure 4:
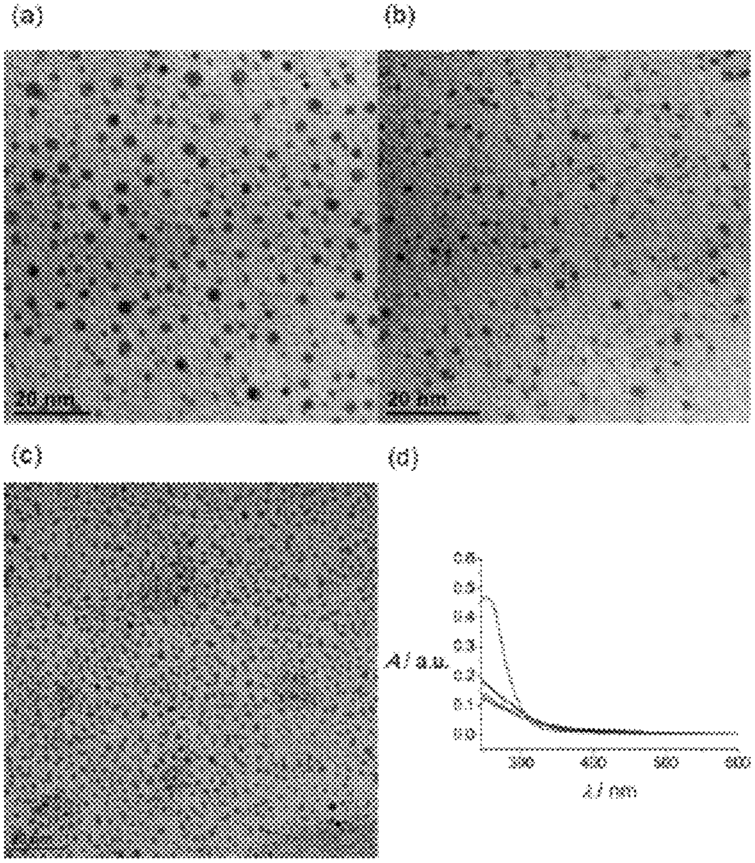
FIG. 4. (a) Transmission electron microscopy (TEM) image of Cys1@Pt particles. (b) TEM image of Cys1.1@Pt particles. (c) TEM image of NAC@Pt particles. (d) Ultraviolet/visible (UV/vis) absorbance in water of hexachloroplatinic acid (top curve at origin), Cys1.1@Pt ($2^{nd}$ topmost curve at origin), NAC@Pt ($3^{rd}$ topmost curve at origin) and Cys1@Pt (bottom curve at origin). The absence of an absorbance peak at about 260 nm for the nanoparticle suspensions shows that substantially no platinum ions are present to catalyze a reaction.

FIG. 4 shows TEM images of Cys1@Pt particles, Cys1.1@Pt particles, and NAC@Pt particles, and UV/vis characterization of the particles.

Figure 5:
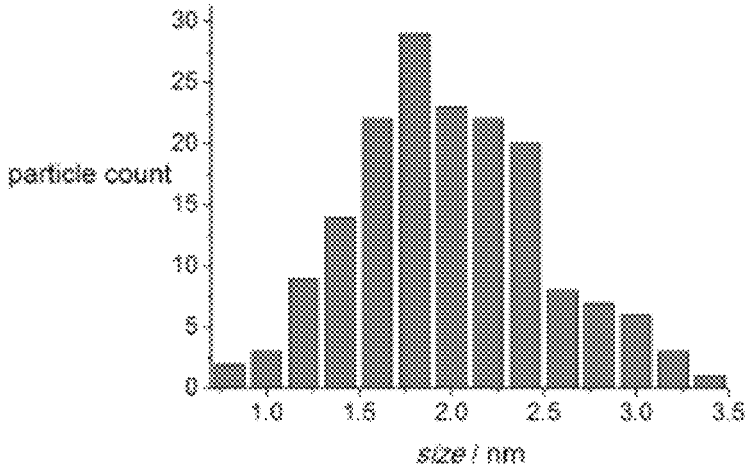
FIG. 5. Nanoparticle size distribution of NAC@Pt.
Figure 6:
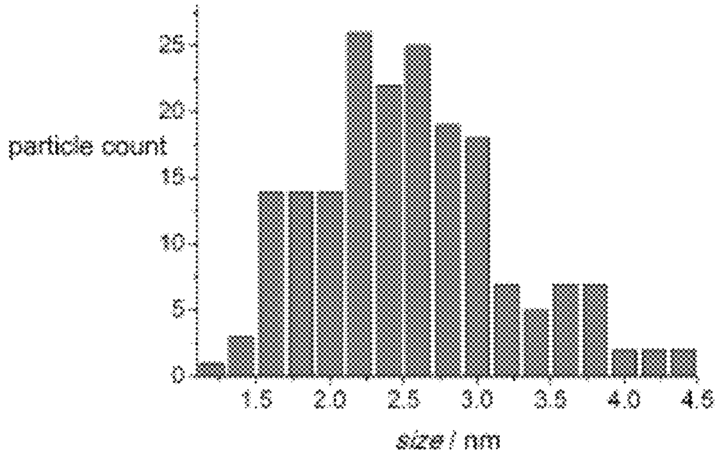
FIG. 6. Nanoparticle size distribution of Cys1@Pt.
Figure 7:
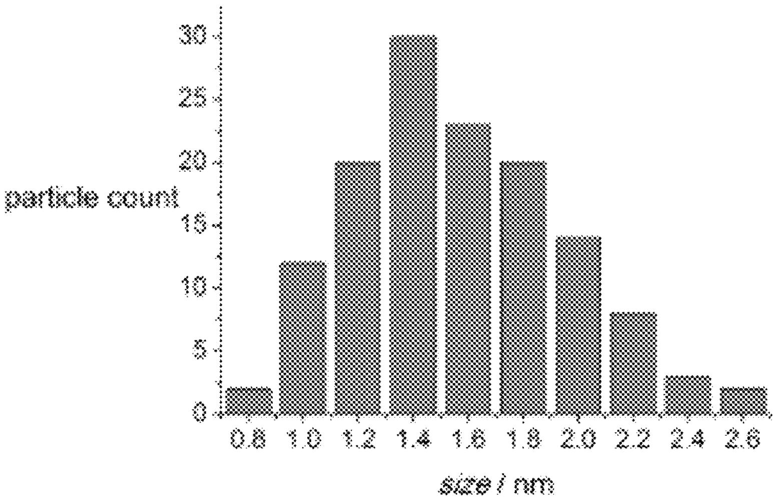
FIG. 7. Nanoparticle size distribution of Cys1.1@Pt.

Particle size distributions were determined for the three different particles. For NAC@Pt, Cys1@Pt and Cys1.1@Pt, 169, 187 and 134 particles were chosen at random. Sizes for the different particles of 1.9±0.4 nm, 2.4±0.5 nm and 1.4±0.3 nm were found. The given deviation corresponds to the standard deviation derived from a Gaussian fit over the particle size distribution. Histograms of the size distributions are shown in FIGS. 5-7.

Thermogravimetric Analysis (TGA)

Figure 8:
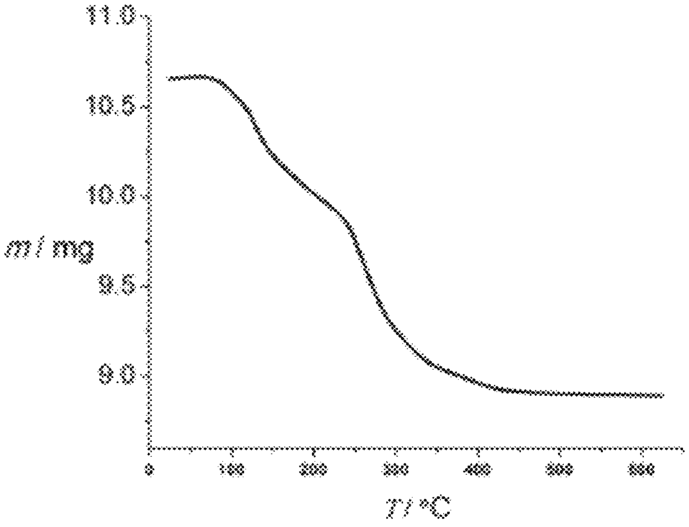
FIG. 8. Thermogravimetric analysis of NAC@Pt.
Figure 9:
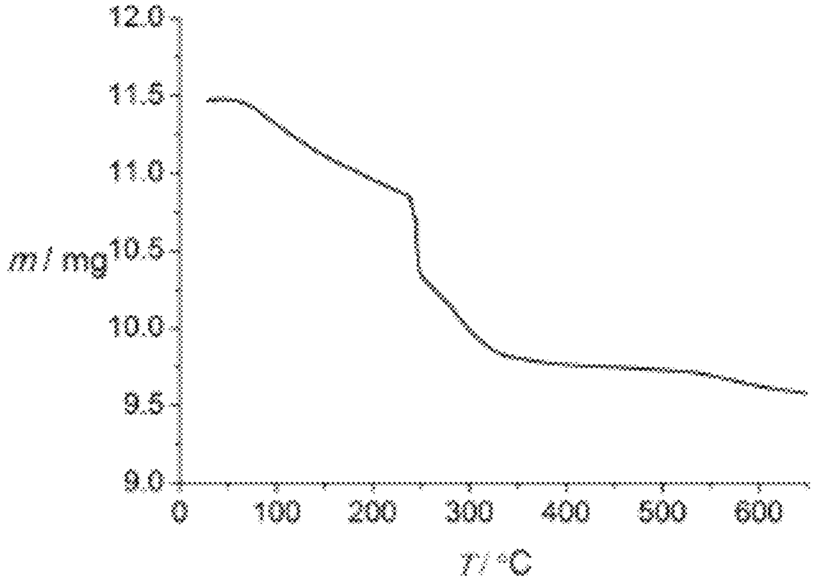
FIG. 9. Thermogravimetric analysis of Cys1 @Pt.
Figure 10:
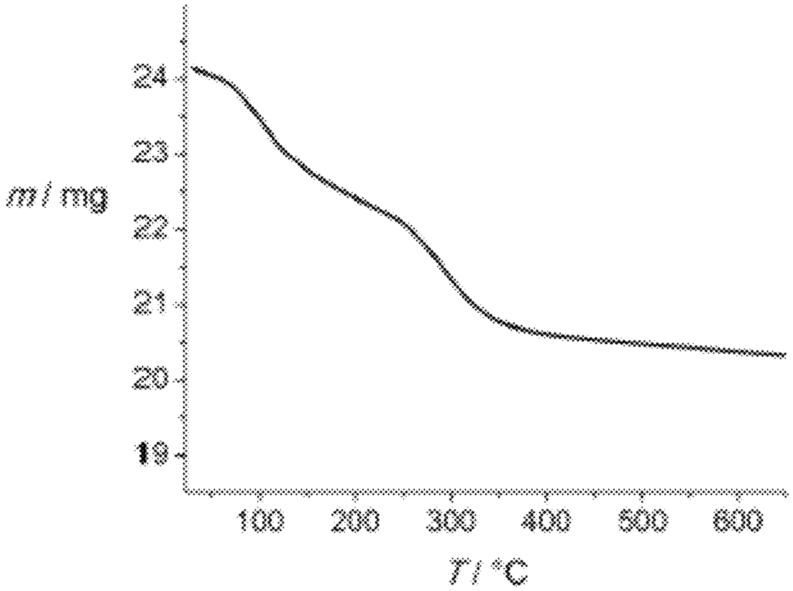
FIG. 10. Thermogravimetric analysis of Cys1.1@Pt.

Thermogravimetric analysis was performed from about 25° C. to about 650° C. under argon. The TGA curves for the three particles are depicted in FIGS. 8-10 and show that the surfaces of all the particles are about 16 wt. % covered.

NMR of the Particles

Figure 11:
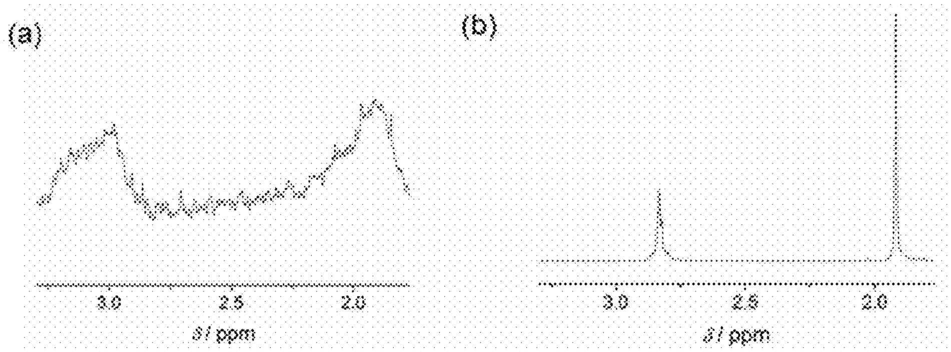
FIG. 11. $^1H$ NMR spectra of (a) NAC@Pt and (b) N-acetylcysteine both in $D_2O$. The line broadening in (a) shows that the ligand is coordinated to the particles' surfaces.
Figure 12:
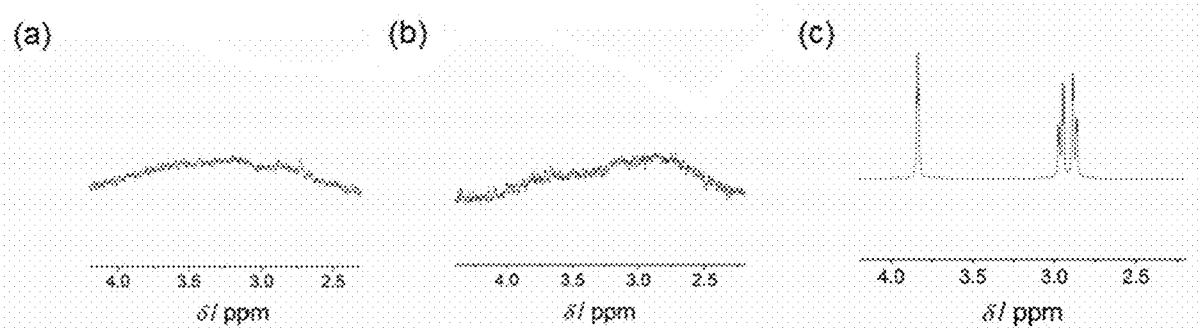
FIG. 12. $^1H$ NMR spectra of (a) Cys1@Pt, (b) Cys1.1@Pt and (c) cysteine in $D_2O$. The line broadening in (a) and (b) shows that the ligand is coordinated to the particles' surfaces.

In order to demonstrate that binding of the ligands to the particles has occurred, $^{1}H$ NMR spectra were recorded at $B_0$=about 14.1 T. A significant dipolar broadening of the peaks was observed due to the coordination to the nanoparticles for all three samples (FIGS. 11-12).

Mercury Poisoning

Figure 13:
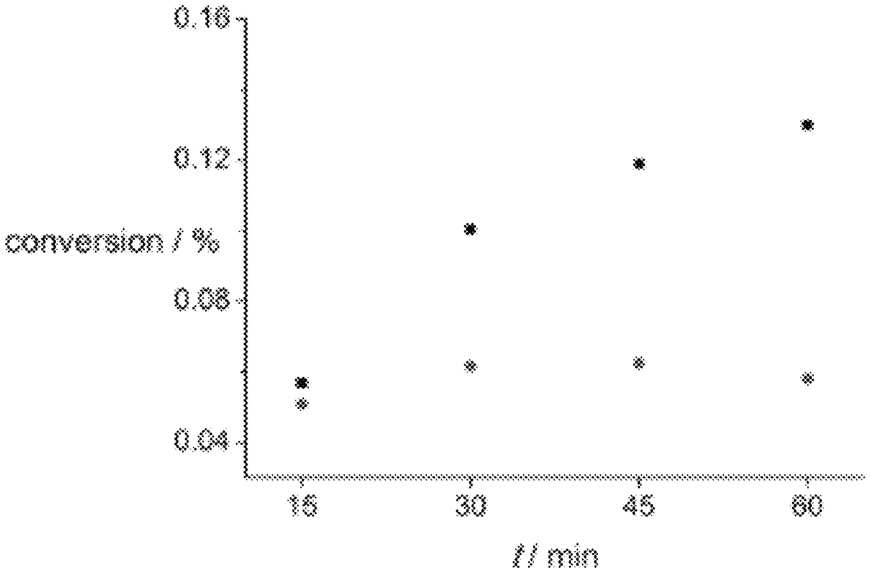
FIG. 13. Mercury poisoning test of NAC@Pt. Without mercury the reaction progresses (squares) whereas the reaction stops upon addition of mercury (circles).
Figure 14:
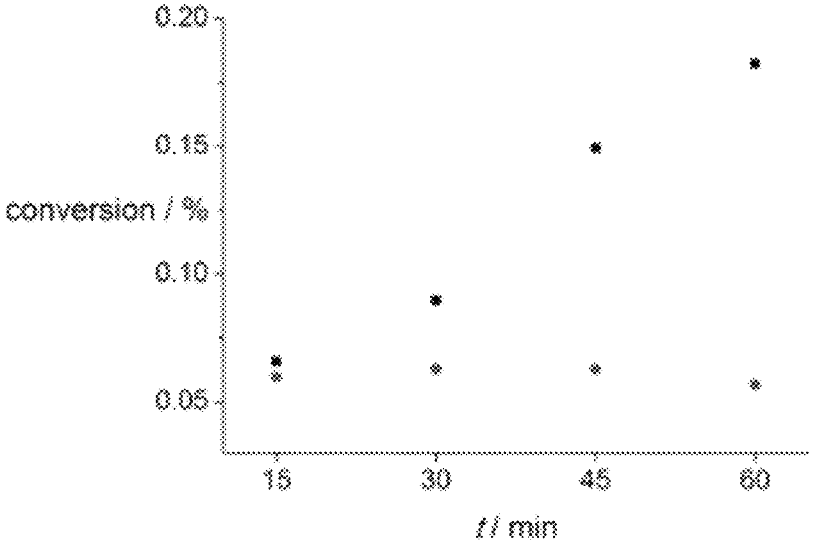
FIG. 14. Mercury poisoning test of Cys1 @Pt. Without mercury the reaction progresses (squares) whereas the reaction stops upon addition of mercury (circles).
Figure 15:
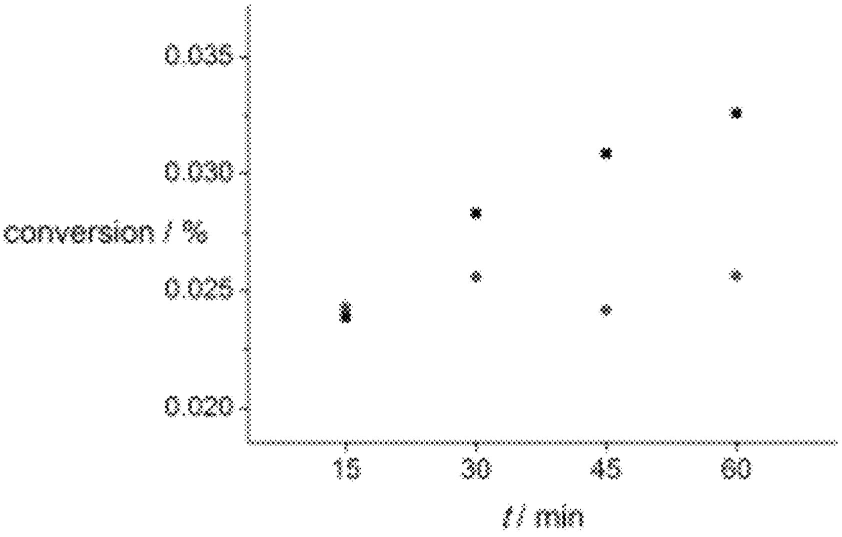
FIG. 15. Mercury poisoning test of Cys1.1@Pt. Without mercury the reaction progresses (squares) whereas the reaction stops upon addition of mercury (circles).

A mercury poisoning test was performed for the nanoparticles. In this experiment, added mercury forms amalgams with the platinum nanoparticles which results in catalytic deactivation. If the reaction is catalyzed by platinum ions rather than the particles, the reaction would progress since no deactivated amalgam is formed. For the test about 2.0 mg of particles were suspended in about 4 mL of water that contained an internal potassium acetate standard and about 0.4 mL hydroxyethyl acrylate was added. Half of the solution was used for the poisoning test and half of it was used to run a control experiment without mercury. In both solutions, hydrogen was bubbled over about 60 minutes with a flow rate of about 100 mL/minute. Into one reaction about 20 μL of mercury was added after about 15 minutes resulting in termination of the hydrogenation, whereas hydrogenation in the control experiment progresses (See FIGS. 13-15). Thus the hydrogenation is catalyzed by the nanoparticles and not residual platinum ions.

Figure 16:
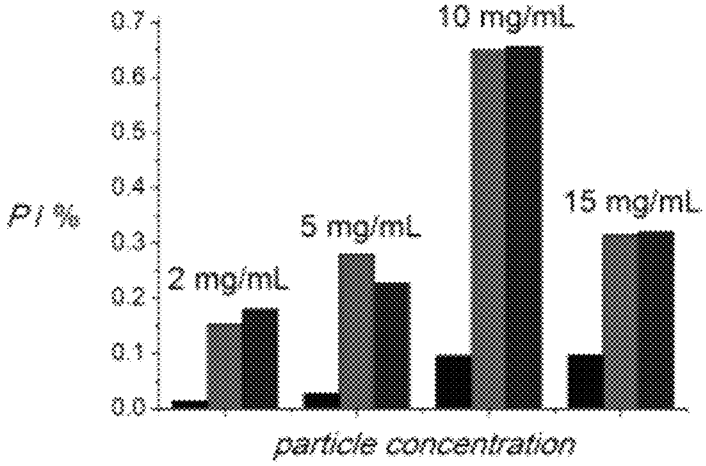
FIG. 16. Polarization as a function of particle concentration: NAC@Pt (left bars), Cys1@Pt (middle bars) and Cys1.1@Pt (right bars).
Figure 17:
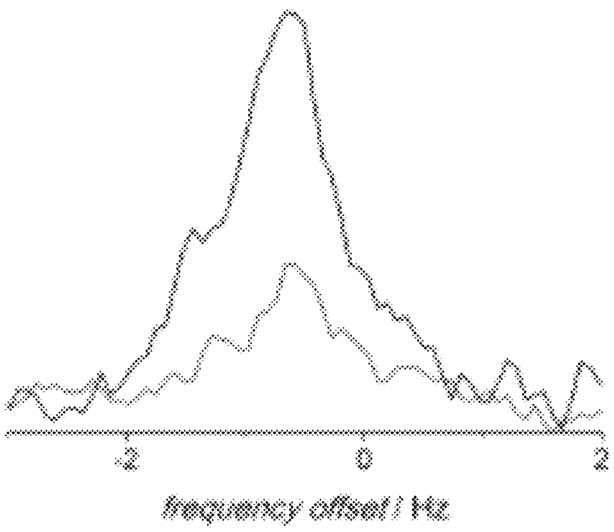
FIG. 17. Thermal polarized signal of $^{13}C$ enriched HEP after 256 scans (top curve) and hyperpolarized signal (bottom curve, ten times magnified).

Para-Hydrogen Experiments $^{1}H$ NMR experiments with para-hydrogen (about 95% para-enriched) were performed on a Bruker AV600 spectrometer ($B_0$=about 14.1 T). Samples were prepared in about 5 mm Young tubes from New Era that have been tested for blind activity before usage. Under inert gas about 2 mg hydroxyethyl acrylate (about 0.04 mmol) and various nanoparticle concentrations were suspended in about 0.5 mL $D_2O$. Each sample was heated to about 80° C., pressurized with about 5 bars of para-hydrogen, shaken in the earth's magnetic field (ALTADENA experiment) and transported into the center of the magnet within about 5 s. The spectrum was recorded in a single scan (45°-pulse). After the hyperpolarization experiment, a spectrum was recorded with the formed product in thermal equilibrium, and the signal enhancement and the corresponding polarization calculated. Various nanoparticle concentrations were used to determine the optimal particle concentration to generate the highest possible polarization and it was found to be about 10 mg/mL for all of the tested particles (FIG. 16). Each experiment was repeated at least 3 times. $^{13}C$ polarization experiments were performed on a custom-built polarizer at Cedars-Sinai Medical Center according to procedures at about 60° C. As before, the $^{13}C$ polarization achieved with the described polarizer was a factor of about 10 higher than in thermal equilibrium. FIG. 17 compares the hyperpolarized signal with a signal in thermal equilibrium after 256 scans, showing that with the current polarizer setup no significant $^{13}C$ polarization could be achieved. Therefore, the construction of an optimized polarizer in conjunction with a heterogeneous catalyst is desirable.

Particle Recycling

Figure 18:
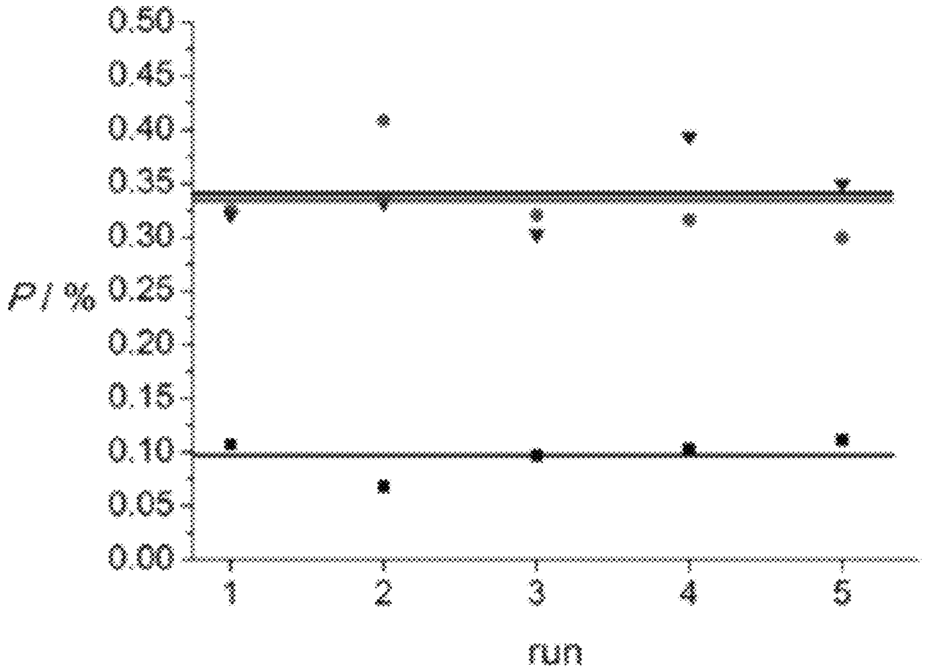
FIG. 18. Particle recycling experiments with Cys1.1@Pt (inverted triangles), Cys1@Pt (circles) and NAC@Pt (squares). The added lines represent the average polarization values achieved with each particle.
Figure 19:
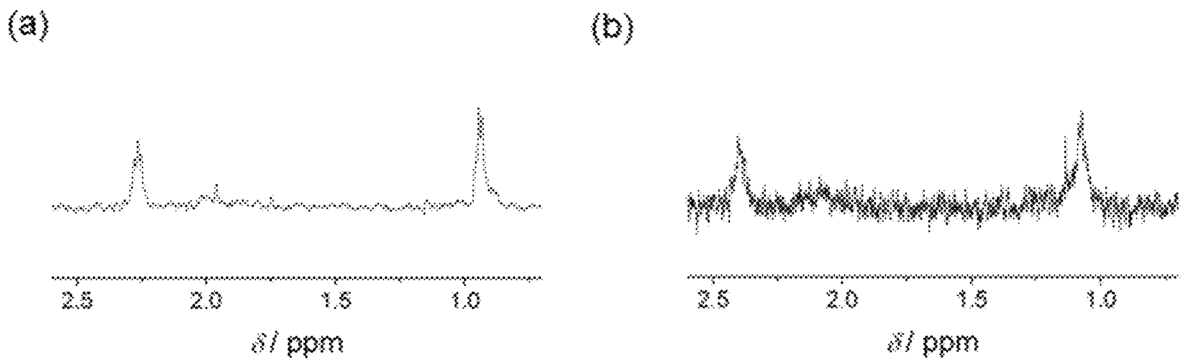
FIG. 19. a) $^1H$ spectrum of a product in a supernatant after separating NAC@Pt and the product in solution at $B_0$=about 14.1 T. b) $^1H$ spectrum of the hyperpolarization experiment after additional HEA was added. The spectrum shows that no hyperpolarization pattern is observable and the thermal magnetization as not fully built up yet. Thus, significant leaching of the catalyst is not observable.
Figure 20:
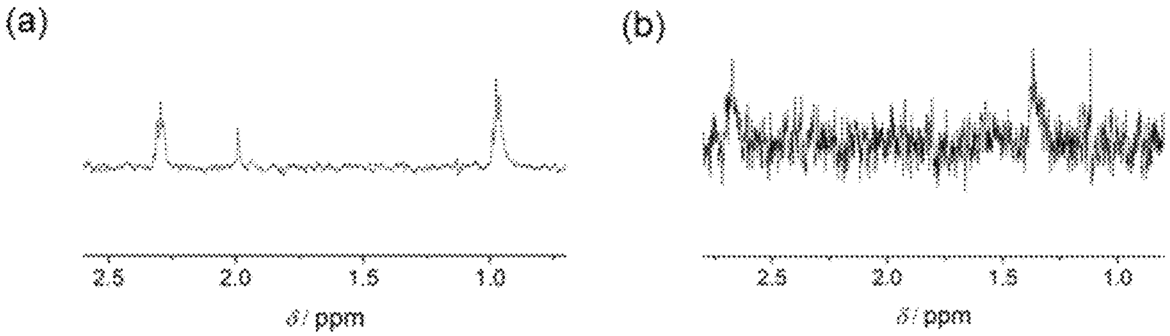
FIG. 20. a) $^1H$ spectrum of a product in a supernatant after separating Cys1@Pt and the product in solution at $B_0$=about 14.1 T. b) $^1H$ spectrum of the hyperpolarization experiment after additional HEA was added. The spectrum shows that no hyperpolarization pattern is observable and the thermal magnetization as not fully built up yet. Thus, significant leaching of the catalyst is not observable.
Figure 21:
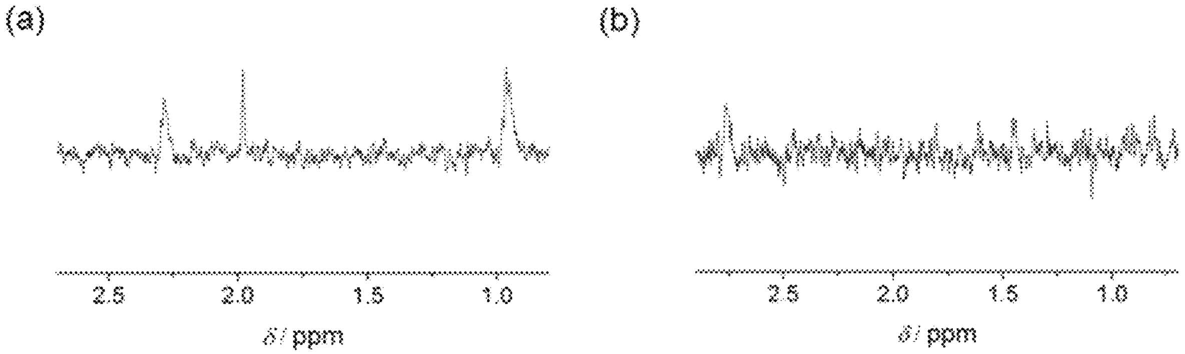
FIG. 21. a) $^1H$ spectrum of a product in a supernatant after separating Cys1.1@Pt and the product in solution at $B_0$=about 14.1 T. b) $^1H$ spectrum of the hyperpolarization experiment after additional HEA was added. The spectrum shows that no hyperpolarization pattern is observable and the thermal magnetization as not fully built up yet. Thus, significant leaching of the catalyst is not observable.

A further proof that the hydrogenation and thus hyperpolarization is catalyzed due to the nanoparticles is a recycling experiment. In this experiment about 15 mg of particles were used to hyperpolarize HEP at about 80° C. and the hyperpolarized signal detected. Afterwards the particles were separated from the supernatant including the hydrogenated product in two different ways: either by centrifuging the particles in $D_2O$ with about 109000 rotations per minute (rpm) for about 2 hours in an ultracentrifuge, or by removing the solvent in vacuum followed by washing the particles with ethanol and drying them under vacuum again. Each of these experiments was performed twice for each type of particle. Afterwards the particles were reused up to four times following the same procedure. Over the course of the five performed experiments no significant loss in polarization was observed (FIG. 18). To ensure that no significant amount of platinum has leached into the supernatant or that no significant platinum ions dissolved in the solvent were causing the hyperpolarized signal, hyperpolarization experiments with the supernatant solvent were performed. To the supernatant from the polarization experiments, about 2 mg HEA were added and a hyperpolarization experiment performed as above was conducted. FIGS. 19-21 show that no hyperpolarized signal could be observed. Therefore, it can be concluded that the polarization was indeed generated due to the platinum nanoparticle catalyst and that no significant leaching has occurred.

As used herein, the singular terms "a," "an," and "the" may include plural referents unless the context clearly dictates otherwise. Thus, for example, reference to an object may include multiple objects unless the context clearly dictates otherwise.

As used herein, the term "set" refers to a collection of one or more objects. Thus, for example, a set of objects can include a single object or multiple objects.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. For example, when used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, a first numerical value can be "substantially" or "about" the same as a second numerical value if the first numerical value is within a range of variation of less than or equal to ±10% of the second numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a range of about 1 to about 200 should be understood to include the explicitly recited limits of about 1 and about 200, but also to include individual values such as about 2, about 3, and about 4, and sub-ranges such as about 10 to about 50, about 20 to about 100, and so forth.

While the disclosure has been described with reference to the specific embodiments thereof, it should be understood by those skilled in the art that various changes may be made and equivalents may be substituted without departing from the true spirit and scope of the disclosure as defined by the appended claims. In addition, many modifications may be made to adapt a particular situation, material, composition of matter, method, operation or operations, to the objective, spirit and scope of the disclosure. All such modifications are intended to be within the scope of the claims appended hereto. In particular, while certain methods may have been described with reference to particular operations performed in a particular order, it will be understood that these operations may be combined, sub-divided, or re-ordered to form an equivalent method without departing from the teachings of the disclosure. Accordingly, unless specifically indicated herein, the order and grouping of the operations are not a limitation of the disclosure.

What is claimed is:

1. A method for inducing hyperpolarization from para-hydrogen, comprising: hydrogenating a substrate, in the presence of ligand-capped nanoparticles and a solvent, by flowing or pressurizing para-hydrogen gas to yield a polarized substrate; and removing the ligand-capped nanoparticles from the polarized substrate, wherein:

the ligand-capped nanoparticles comprise metal nanoparticles that are surface-functionalized with organic ligands having a molecular weight of no greater than 300 g/mol, and the organic ligands each have multiple binding moieties as coordinating sites for binding to a nanoparticle surface;

the metal nanoparticles comprise platinum, palladium, ruthenium, rhodium, or any combination thereof;

the ligands comprise cysteine;

wherein a surface coverage of the metal nanoparticles by the organic ligands is at least 4.2 ligands per $nm^2$; and the metal nanoparticles are bound to larger-sized particles or immobilized on a solid support.

2. The method of claim 1, wherein the metal nanoparticles comprise platinum.

3. The method of claim 1, wherein the molecular weight of the organic ligands is no greater than 250 g/mol.

4. The method of claim 1, wherein a concentration of the ligand-capped nanoparticles in the solvent is in a range of 1 mg/mL to 20 mg/mL.

5. The method of claim 1, wherein the organic ligands each includes a sulfhydryl group and an amino group as the binding moieties.

6. The method of claim 1, wherein the organic ligands each further includes at least one hydrophilic moiety.

7. The method of claim 1, wherein the hydrophilic moiety is a carboxyl group.

8. The method of claim 1, wherein the solvent is water or heavy water ($D_2O$).

9. The method of claim 1, wherein the solvent is water.

10. The method of claim 1, wherein the nanoparticles have an average size in a range of 0.5 nm to 10 nm.

11. The method of claim 1, wherein removing the ligand-capped nanoparticles is performed by filtration.

12. A method for medical imaging, comprising:

performing the method for inducing hyperpolarization from para-hydrogen of claim 1;

conveying the hyperpolarized substrate to a patient; and performing in vivo imaging of the hyperpolarized substrate conveyed to the patient.

13. The method of claim 12, wherein the in vivo imaging comprises MRI.

* * * * *